(12) United States Patent
Chen

(10) Patent No.: US 9,038,627 B2
(45) Date of Patent: May 26, 2015

(54) ARTIFICIAL ORAL AIRWAY, ESOPHAGEAL BLOCKER, AND PHARYNGEAL AIRWAY ASSEMBLY

(76) Inventor: Tien-Sheng Chen, Taipei (TW)

( * ) Notice: Subject to any disclaimer, the term of this patent is extended or adjusted under 35 U.S.C. 154(b) by 584 days.

(21) Appl. No.: 13/366,423

(22) Filed: Feb. 6, 2012

(65) Prior Publication Data
US 2013/0098366 A1   Apr. 25, 2013

(30) Foreign Application Priority Data
Oct. 21, 2011 (TW) .............................. 100138334 A

(51) Int. Cl.
*A61M 16/04* (2006.01)

(52) U.S. Cl.
CPC ........... *A61M 16/04* (2013.01); *A61M 16/0409* (2014.02); *A61M 16/0427* (2014.02); *A61M 16/0431* (2014.02)

(58) Field of Classification Search
CPC ............ A61M 16/00; A61M 16/0488; A61M 2016/0493; A61M 16/04; A61M 16/0402; A61M 16/0497; A61M 2210/1028
See application file for complete search history.

(56) References Cited

U.S. PATENT DOCUMENTS

| | | | | |
|---|---|---|---|---|
| 4,919,126 A * | 4/1990 | Baildon | ................... | 128/207.14 |
| 5,720,275 A * | 2/1998 | Patil et al. | ................ | 128/200.26 |
| 5,819,733 A * | 10/1998 | Bertram | ................... | 128/207.15 |
| 6,196,224 B1 * | 3/2001 | Alfery | ....................... | 128/207.14 |
| 6,626,169 B2 * | 9/2003 | Gaitini | ..................... | 128/200.14 |
| 6,672,305 B2 * | 1/2004 | Parker | ...................... | 128/200.26 |
| 2002/0040712 A1 * | 4/2002 | Chou | ........................ | 128/200.26 |
| 2009/0013995 A1 * | 1/2009 | Williams | ................. | 128/200.26 |
| 2010/0132700 A1 * | 6/2010 | Filipi et al. | ............... | 128/200.26 |
| 2010/0170506 A1 * | 7/2010 | Pawels et al. | ............ | 128/200.26 |
| 2010/0199998 A1 * | 8/2010 | Matioc | .................... | 128/207.14 |
| 2011/0126840 A1 | 6/2011 | Ogilvie et al. | | |

* cited by examiner

*Primary Examiner* — Tan-Uyen (Jackie) T Ho
*Assistant Examiner* — Eric Bryant
(74) *Attorney, Agent, or Firm* — Alan D. Kamrath

(57) ABSTRACT

An artificial oral airway, an esophageal blocker, and a pharyngeal airway assembly are disclosed. The artificial oral airway includes a main body and an airway. The airway penetrates the main body, and the main body has a body front end. The esophageal blocker is slidably connected to the artificial oral airway and penetrates the main body to contact the esophagus of a patient. The esophageal blocker has an opening portion, an esophageal blocking portion, and a slice body. The opening portion touches the body front end, and the esophageal blocking portion is used for blocking the esophagus of the patient. The slice body is used for connecting the opening portion and the esophageal blocking portion.

4 Claims, 6 Drawing Sheets

ARTIFICIAL ORAL AIRWAY, ESOPHAGEAL BLOCKER, AND PHARYNGEAL AIRWAY ASSEMBLY

BACKGROUND OF THE INVENTION

1. Field of the Invention

The present invention relates to a medical device. More specifically, the present invention relates to an artificial oral airway, an esophageal blocker, and a pharyngeal airway assembly.

2. Description of the Related Art

For apnea patients, the top priority for emergency medical personnel is to sustain the pulmonary gas supply. Among the various respiration sustaining instruments, the laryngeal mask airway (LMA) is a common alternative to endotracheal intubation due to its ease of operability. However, the laryngeal mask airway is soft and not easy to operate. In addition, because the shape of the front end of the laryngeal mask airway is usually circular or elliptical, and when the laryngeal mask airway enters the throat of a patient, the front end of the laryngeal mask airway is deformed by the pressing of the larynx, consequently leading to failure in placement.

The artificial oral airway assembly disclosed in US Patent Publication number 20110126840 is an artificial oral airway that is placed in the mouth of a patient first, and, then, the slice body is placed inside the artificial oral airway to uplift the tongue of the patient. However, this kind of artificial oral airway assembly can only uplift the tongue of a patient. If the patient needs oxygen, an extra endotracheal tube has to be added, which causes inconvenience to the user.

Therefore, there is a need to provide a new artificial oral airway assembly to obviate the problems of the prior art.

SUMMARY OF THE INVENTION

It is an object of the present invention to provide an artificial oral airway, an esophageal blocker, and a pharyngeal airway assembly, all of which can be placed into a patient easily.

To achieve the abovementioned object, the pharyngeal airway assembly of the present invention comprises an artificial oral airway and an esophageal blocker. The artificial oral airway comprises a main body, an airway, and at least one blocking strip. The airway passes through the main body. The at least one blocking strip is mounted at a main body rear end. The esophageal blocker is slidably connected to the artificial oral airway, passes through the airway, and touches the esophageal inlet of the patient. The esophageal blocker comprises an opening part, an esophageal blocker part, and a slice body. The opening part touches a main body front end, and the esophageal blocker part is used for blocking the esophageal inlet of the patient. The slice body is used for connecting to the opening part and the esophageal blocker part.

According to one embodiment of the present invention, there are two blocking strips employed in the artificial oral airway of the present invention.

According to one embodiment of the present invention, the esophageal blocker part of the esophageal blocker of the present invention comprises two blocking portions and an indentation. The indentation is located between the two blocking portions.

DETAILED DESCRIPTION OF THE PREFERRED EMBODIMENTS

The advantages and innovative features of the invention will become more apparent from the following detailed descriptions when taken together with the accompanying drawings.

Figure 1:
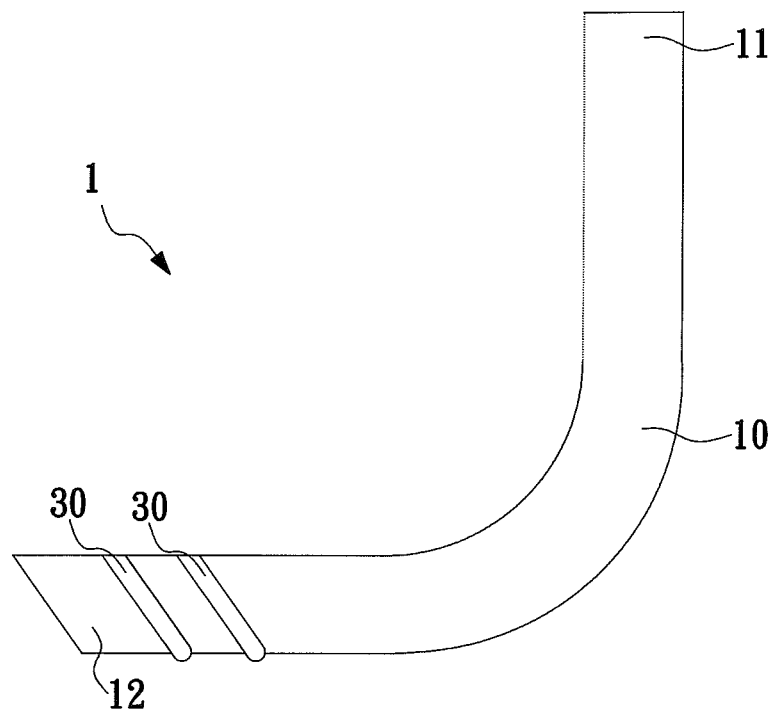
FIG. 1 illustrates a lateral view of the artificial oral airway of the present invention.
Figure 2:
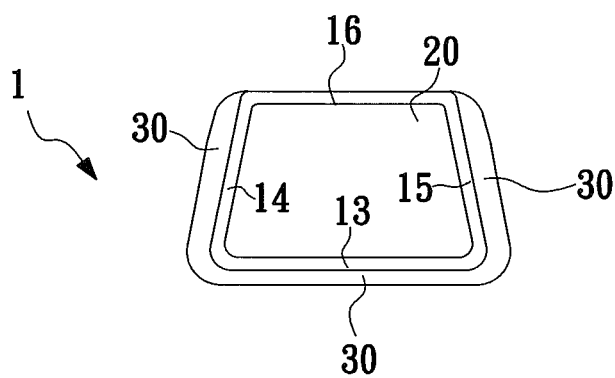
FIG. 2 illustrates a cross-sectional schematic drawing of the artificial oral airway of the present invention.

Please refer to FIG. 1 and FIG. 2, which are related to one embodiment of the artificial oral airway of the present invention. FIG. 1 illustrates a lateral view of the artificial oral airway of the present invention, and FIG. 2 illustrates a cross-sectional schematic drawing of the artificial oral airway of the present invention.

As shown in FIG. 1 and FIG. 2, the artificial oral airway 1 of the present invention comprises a main body 10, an airway 20, and at least one blocking strip 30. The main body 10 comprises a main body front end 11 and a main body rear end 12. The airway 20 passes through the main body 10. The at least one blocking strip 30 is mounted at the main body rear end 12. It is noted that, according to one embodiment of the present invention, as shown in FIG. 1, the shape of the main body 10 of the present invention is a curve which is curved from the main body front end 11 to the main body rear end 12, and its curvature matches the curvature of a human's oral cavity. There are two blocking strips 30 employed in the artificial oral airway 1 of the present invention, and the blocking strip 30 is made of elastic plastics or silicon. However, the present invention is not limited to this embodiment, and the number of the blocking strip 30 can be one or more.

As shown in FIG. 2, the main body 10 of the artificial oral airway 1 of the present invention further comprises a bottom surface 13, a first side surface 14, a second side surface 15, and a top surface 16, all of which together form the four surfaces of the main body 10. The first side surface 14 corresponds to the second side surface 15 and is connected to the bottom surface 13 and the top surface 16. The two blocking strips 30 are mounted at the bottom surface 13, the first side surface 14, and the second side surface 15. It is noted that the size of the main body 10 may vary and depends on the height and the weight of the patient. The cross sectional area of the main body 10, i.e., the area surrounded by the bottom surface 13, the first side surface 14, the second side surface 15, and the top surface 16, matches the cross sectional area of the throat of the patient, such that the main body 10 can firmly contact the throat of the patient, and such that the isolating feature of the blocking strip 30 on the main body 10 is also enhanced. As shown in FIG. 2, the blocking strip 30 is mounted on the bottom surface 13, the first side surface 14, and the second side surface 15. The top surface 16 touches the tongue of the patient, and the blocking strip 30 is not mounted on the top surface 16. However, the present invention is not limited to the above-mentioned embodiment.

Figure 3:
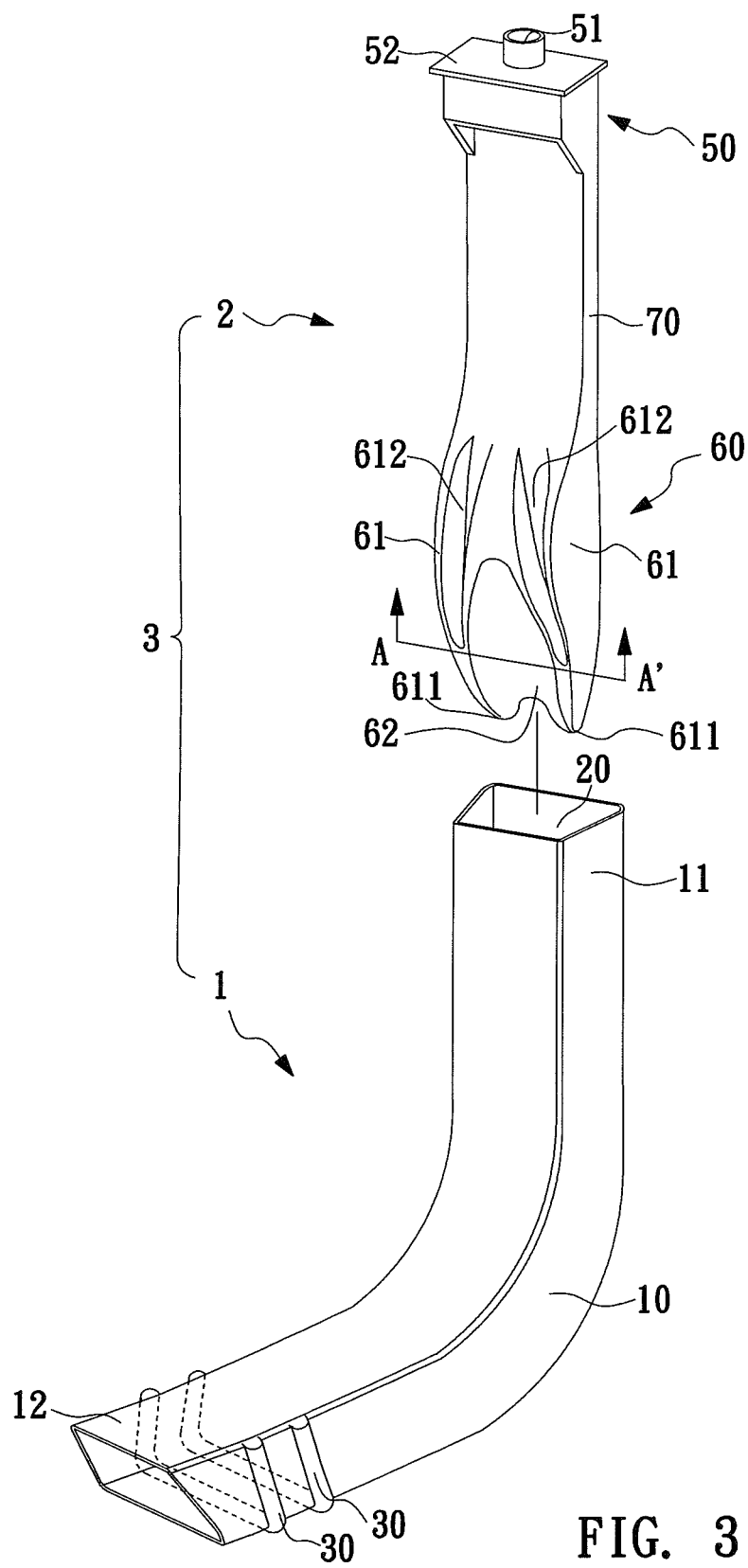
FIG. 3 is a schematic drawing of the pharyngeal airway assembly of the present invention.
Figure 3A:
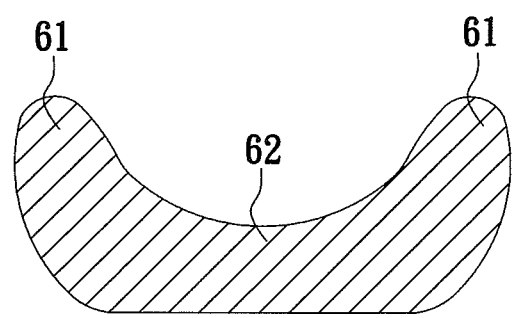
FIG. 3a is a cross-sectional view in the direction AA' in FIG. 3.

Please refer to FIG. 3 and FIG. 3a, which are related to one embodiment of the pharyngeal airway assembly of the present invention. FIG. 3 is a schematic drawing of the pharyngeal airway assembly of the present invention, and FIG. 3a is a cross-sectional view in the direction AA' in FIG. 3.

As shown in FIG. 3, the pharyngeal airway assembly 3 of the present invention comprises an artificial oral airway 1 and an esophageal blocker 2. The esophageal blocker 2 is slidably connected to the artificial oral airway 1, such that it can pass through the airway 20 and contact the esophageal inlet of the patient. The esophageal blocker 2 comprises an opening part 50, an esophageal blocker part 60, and a slice body 70. After, the esophageal blocker 2 is connected to the artificial oral airway 1, the opening part 50 touches the main body front end 11. The esophageal blacker part 60 blocks the esophageal inlet of the patient. As shown in FIGS. 3 and 4-5a, the slice body 70 is in a sheet-like shape having first and second, parallel, spaced surfaces and first and second, spaced sides extending between and interconnecting the first and second, parallel, spaced surfaces. The slice body 70 is used for connecting the opening part 50 and an esophageal blocker part 60.

According to one embodiment of the present invention, as shown in FIG. 3, the opening part 50 comprises an air vent 51 and a blocking unit 52. The air vent 51 is located on the blocking unit 52. The esophageal blocker part 60 further comprises two blocking portions 61 and an indentation 62. The indentation 62 is located between the two blocking portions 61. It is noted that the shape of each blocking portion 61 is substantially similar to the shape of an uprising hill. The raised height and the scope of the rising height of each blocking portion 61 are sufficient to cover the esophageal inlet of the patient. Furthermore, the cross-sectional view of the esophageal blocker part 60 is shown in FIG. 3a. Because the indentation 62 is situated between the two blocking portions 61, the cross-section of the esophageal blocker part 60 has height differences, and the cross-section shows a height order of high-low-high from left to the right. This high-low-high feature matches the physical structure of a human's throat, such that the esophageal blocker part 60 can smoothly slide into the esophageal inlet and avoid damaging the upper respiratory tissue during insertion.

Figure 4:
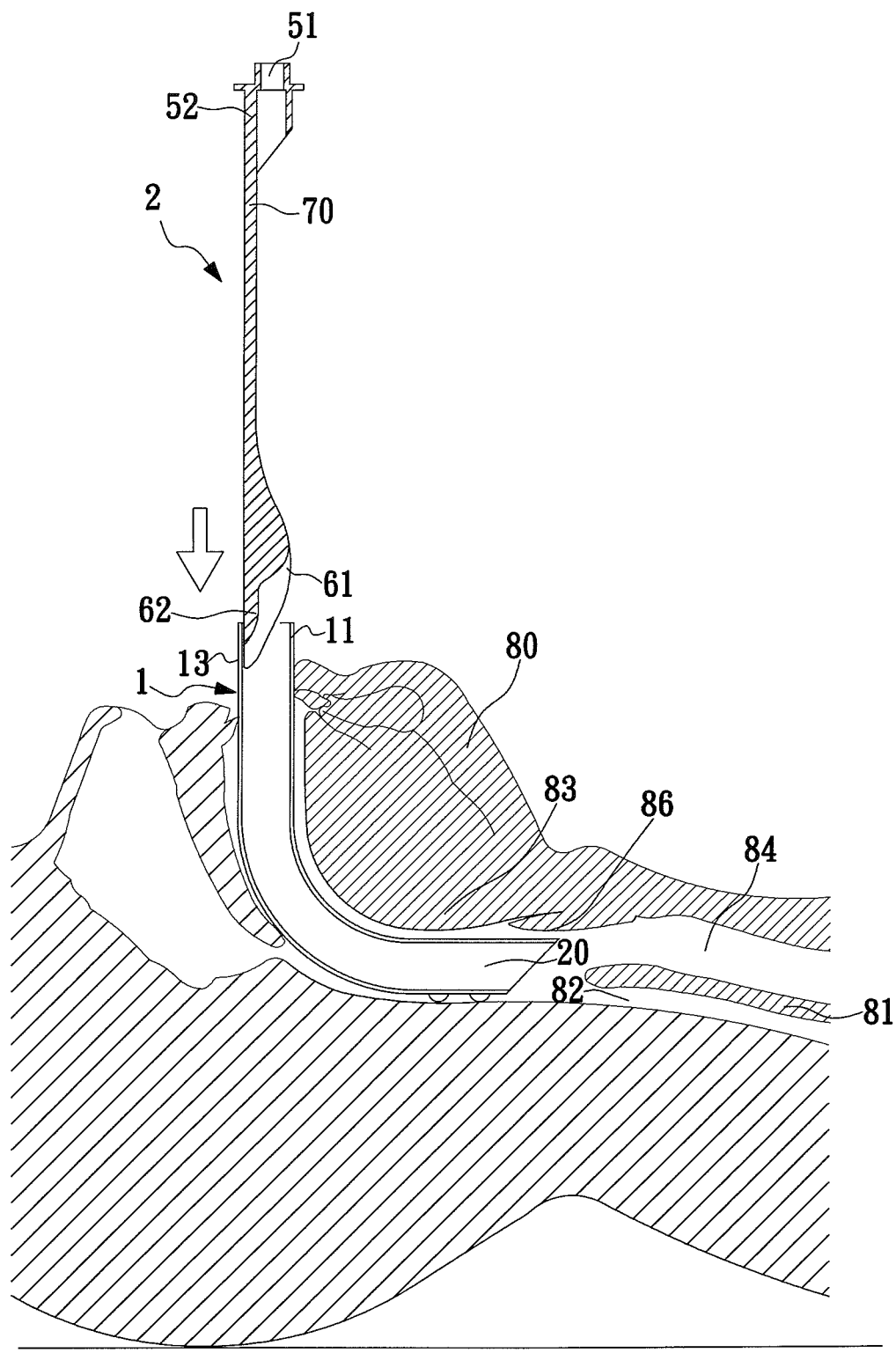
FIG. 4 is one schematic drawing of the usage state of the pharyngeal airway assembly of the present invention.
Figure 5:
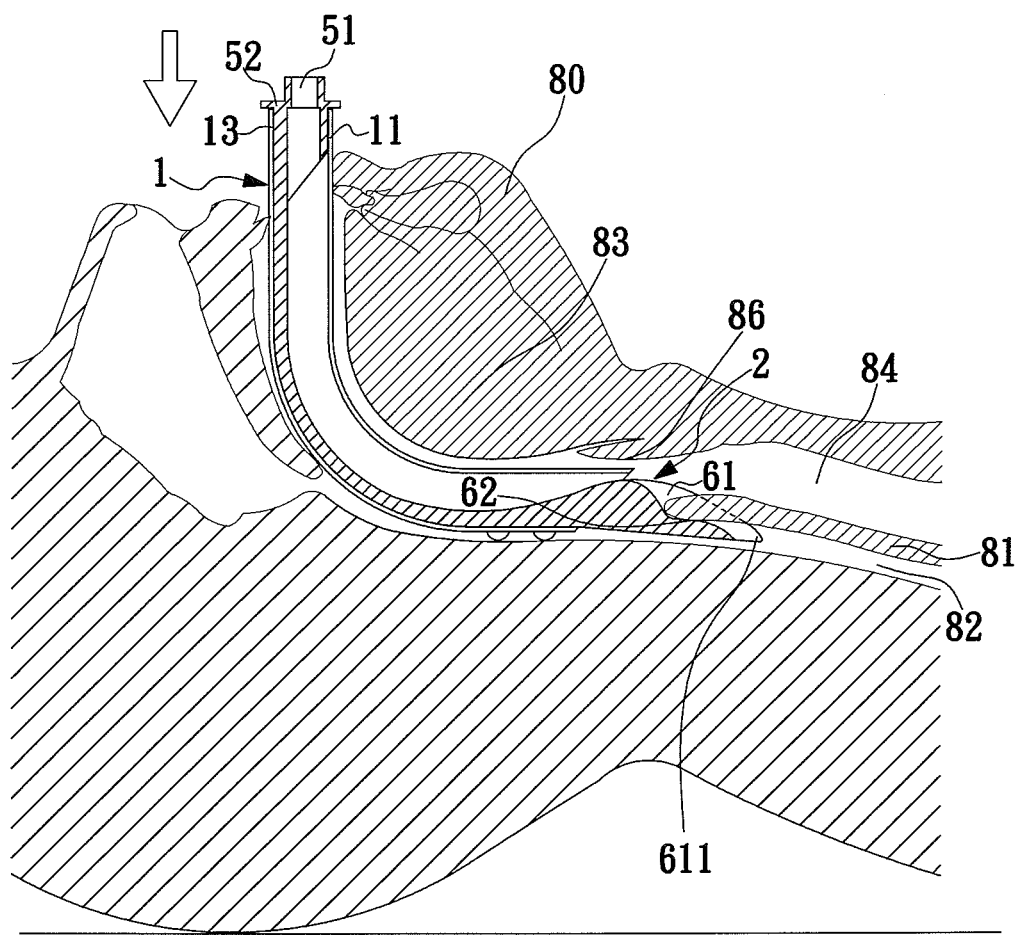
FIG. 5 is another schematic drawing of the usage state of the pharyngeal airway assembly of the present invention.
Figure 5A:
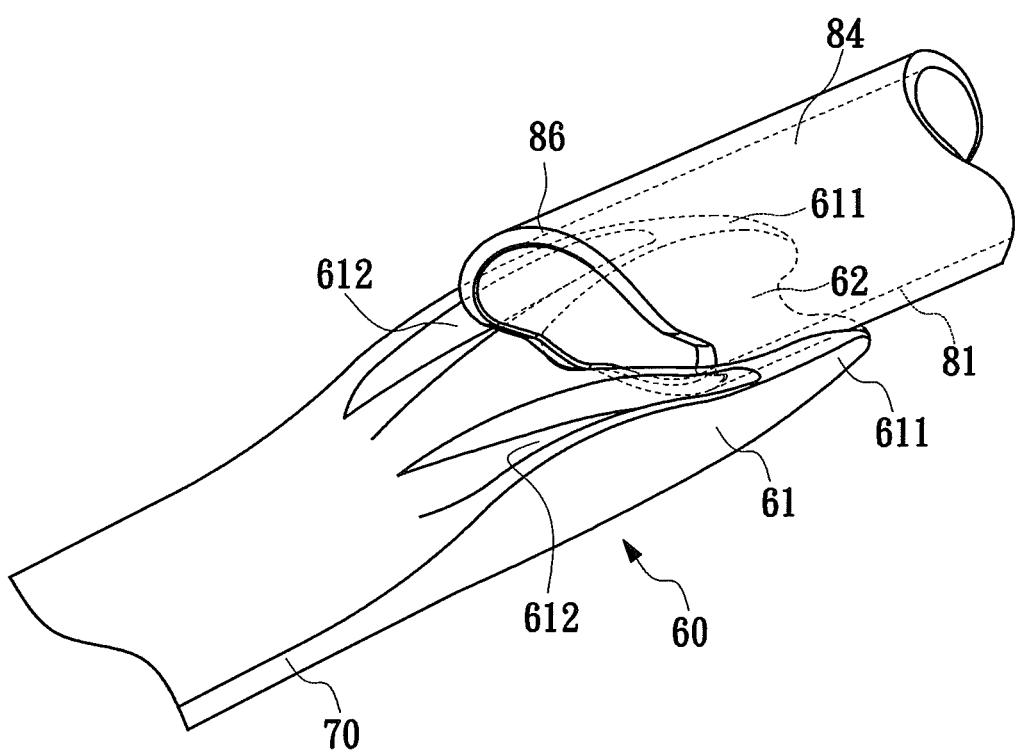
FIG. 5a is a schematic drawing of the esophageal blocker of the present invention combined with the larynx.

Please refer to FIG. 4, FIG. 5, and FIG. 5a. FIG. 4 is one schematic drawing of the usage state of the pharyngeal airway assembly of the present invention, FIG. 5 is another schematic drawing of the usage state of the pharyngeal airway assembly of the present invention, and FIG. 5a is a schematic drawing of the esophageal blocker of the present invention combined with the trachea.

As shown in FIG. 4, while the pharyngeal airway assembly 3 of the present invention is used, the artificial oral airway 1 of the present invention has to be placed into the mouth of the patient 80 first to uplift the tongue 83 of the patient 80 by using the artificial oral airway 1 of the present invention to prevent the larynx from being blocked by the tongue 83. It is noted that after the artificial oral airway 1 of this embodiment is placed into the mouth, the main body rear end 12 of the artificial oral airway 1 is situated roughly beneath the middle of the epiglottis 86 of the patient 80. However, the present invention is not limited to this embodiment. After the artificial oral airway 1 of the present invention is placed in that position, the esophageal blocker 2 of the present invention is placed into the artificial oral airway 1 from the main body front end 11 and moves along the direction indicated in FIG. 4 to form the state illustrated in FIG. 5. It is noted that when the esophageal blocker 2 connects to the artificial oral airway 1, the esophageal blocker 2 slides along the bottom surface 13 of the main body 10.

As shown in FIG. 5, after the esophageal blocker 2 enters the artificial oral airway 1, the esophageal blocker part 60 is slid toward the esophageal inlet 82 along the larynx of the patient 80. Consequently, the blocking portions 61 cover the esophageal inlet 82, the blocking portion front end 611 of the blocking portion 61 enters the esophageal inlet 82, and the rear laryngeal wall 81 of the patient 80 touches the indentation 62, as shown in FIG. 5a. After the esophageal blocker 2 enters the artificial oral airway 1, the blocking unit 52 of the opening part 50 touches the main body front end 11 of the artificial oral airway 1. An external air vent can be connected to the air vent 51 by medical personnel to allow oxygen to pass through the artificial oral airway 1 to enter the trachea 84 to provide an oxygen supply for the patient 80. Because the esophageal inlet 82 of the patient 80 has been covered by the esophageal blocker part 60, the oxygen cannot enter the esophagus. Meanwhile, food inside the stomach of the patient 80 cannot backflow from the esophagus to the trachea causing choking. Furthermore, in order to facilitate entry to place the blocking portion 61 into the esophagus of the patient 80, the two blocking portions 61 further comprise a groove 612 to provide a deforming space for the blocking portion 61 to adjust to the different esophageal inlets of different patients. Moreover, a thin portion can be added at a side of the slice body 70, that is connected to the two blocking portions 61, such that the esophageal blocker 2 can turn easily while passing through the artificial oral airway 1.

To sum up, when the pharyngeal airway assembly 3 of the present invention is used, the artificial oral airway 1 is placed into the mouth of the patient 80 to uplift the tongue 83, and, then, the esophageal blocker 2 is placed into the mouth of the patient 80 along the artificial oral airway 1. When the placement of the esophageal blocker 2 is completed, oxygen can be supplied via the air vent 51 to the patient 80. In addition, the esophageal blocker part 60 of the esophageal blocker 2 can prevent oxygen from entering the esophagus or food from back flowing.

It must be noted that the above-mentioned embodiments are only for illustration. It is intended that the present invention covers modifications and variations of this invention provided that they fall within the scope of the following claims and their equivalents. Therefore, it will be apparent to those skilled in the art that various modifications can be made to the structure of the present invention without departing from the scope or spirit of the invention.

What is claimed is:

1. A pharyngeal airway assembly comprising:
   a main body comprising:
      a main body front end;
      a main body rear end;
      a bottom surface, a first side surface, a second side surface, and a top surface, wherein the first side surface corresponds to the second side surface and is connected to the bottom surface and the top surface, wherein the top surface is adapted to touch a tongue of a patient;
      at least one blocking strip mounted on the bottom surface, the first side surface, and the second side surface at the main body rear end of the main body; and
      an airway passing through the main body; and
   an esophageal blocker slidably received along the bottom surface in the airway and adapted to touch an esophageal inlet of the patient, wherein the esophageal blocker part comprises:
      an opening part touching the main body front end;
      an esophageal blocker part adapted to block the esophageal inlet of the patient;

a slice body connecting the opening part and the esophageal blocker part, wherein the slice body is in a sheet-like shape having first and second, parallel, spaced surfaces and first and second spaced sides extending between and interconnecting the first and second, parallel, spaced surfaces; and two blocking portions and an indentation, wherein the indentation is situated between the two blocking portions, wherein the two blocking portions are adapted to cover the esophageal inlet and the indentation is adapted to touch a rear laryngeal wall of the patient when the esophageal blocker enters a mouth of the patient.

2. The pharyngeal airway assembly as claimed in claim 1, wherein the two blocking portions individually further comprise a blocking portion front end, and wherein each blocking portion front end is adapted to enter the esophageal inlet when the esophageal blocker enters the mouth of the patient.

3. The pharyngeal airway assembly as claimed in claim 2, wherein shapes of each of the two blocking portions are substantially similar to a shape of an uprising hill.

4. The pharyngeal airway assembly as claimed in claim 3, wherein the opening part further comprises an air vent and a blocking unit, wherein the air vent is situated on the blocking unit.

\* \* \* \* \*